(12) United States Patent
Kolter et al.

(10) Patent No.: US 11,993,759 B2
(45) Date of Patent: May 28, 2024

(54) SOLID SOLUTIONS OF ODORIFEROUS SUBSTANCES AND FLAVORING AGENTS WITH VINYL LACTAM POLYMERS

(71) Applicant: BASF SE, Ludwigshafen am Rhein (DE)

(72) Inventors: Karl Kolter, Limburgerhof (DE); Ralf Pelzer, Fuerstenberg (DE); Matthias Karl, Mannheim (DE)

(73) Assignee: BASF SE (DE)

( * ) Notice: Subject to any disclaimer, the term of this patent is extended or adjusted under 35 U.S.C. 154(b) by 705 days.

(21) Appl. No.: 15/768,642

(22) PCT Filed: Oct. 13, 2016

(86) PCT No.: PCT/EP2016/074566
§ 371 (c)(1),
(2) Date: Apr. 16, 2018

(87) PCT Pub. No.: WO2017/067841
PCT Pub. Date: Apr. 27, 2017

(65) Prior Publication Data
US 2018/0305636 A1   Oct. 25, 2018

(30) Foreign Application Priority Data
Oct. 23, 2015   (EP) .................... 15191156

(51) Int. Cl.
| | | |
|---|---|---|
| *A61K 8/02* | (2006.01) | |
| *A23L 27/00* | (2016.01) | |
| *A23L 27/20* | (2016.01) | |
| *A61K 8/34* | (2006.01) | |
| *A61K 8/81* | (2006.01) | |
| *A61K 9/20* | (2006.01) | |
| *A61K 47/10* | (2017.01) | |
| *A61K 47/32* | (2006.01) | |
| *A61K 47/34* | (2017.01) | |
| *A61K 47/46* | (2006.01) | |
| *A61L 9/01* | (2006.01) | |
| *A61Q 13/00* | (2006.01) | |
| *C11B 9/00* | (2006.01) | |
| *C11D 3/00* | (2006.01) | |
| *C11D 3/37* | (2006.01) | |
| *C11D 3/50* | (2006.01) | |

(52) U.S. Cl.
CPC ........ *C11B 9/0015* (2013.01); *A23L 27/2026* (2016.08); *A23L 27/203* (2016.08); *A23L 27/74* (2016.08); *A61K 8/0287* (2013.01); *A61K 8/34* (2013.01); *A61K 8/817* (2013.01); *A61K 8/8182* (2013.01); *A61K 47/10* (2013.01); *A61K 47/32* (2013.01); *A61K 47/34* (2013.01); *A61K 47/46* (2013.01); *A61L 9/01* (2013.01); *A61Q 13/00* (2013.01); *C11B 9/0034* (2013.01); *C11D 3/00* (2013.01); *C11D 3/3776* (2013.01); *C11D 3/3788* (2013.01); *C11D 3/505* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,448,789 A | 5/1984 | Yang |
| 6,423,256 B1 | 7/2002 | Kothrade et al. |
| 2005/0227905 A1 | 10/2005 | Heinz et al. |
| 2008/0293828 A1 | 11/2008 | Bouillo et al. |
| 2009/0301504 A1 | 12/2009 | Worthen et al. |
| 2010/0204425 A1 | 8/2010 | Mertoglu et al. |
| 2012/0146255 A1 | 6/2012 | Maschke et al. |
| 2012/0202894 A1* | 8/2012 | Kolter .............. A61K 47/34 514/772.2 |
| 2015/0216798 A1* | 8/2015 | Cifter .............. A61K 9/2054 424/482 |

FOREIGN PATENT DOCUMENTS

| | | |
|---|---|---|
| CN | 102085344 A | 6/2011 |
| EP | 0 998 919 A2 | 5/2000 |
| EP | 2 463 327 A2 | 6/2012 |
| WO | WO-2007/051743 A2 | 5/2007 |
| WO | WO-2009/013202 A1 | 1/2009 |
| WO | WO-2011/033085 A1 | 3/2011 |

OTHER PUBLICATIONS

International Search Report for PCT Patent Application No. PCT/EP2016/074566, dated Jan. 18, 2017.

* cited by examiner

*Primary Examiner* — Brian Gulledge
(74) *Attorney, Agent, or Firm* — Faegre Drinker Biddle & Reath LLP

(57) ABSTRACT

An optically clear, solid water-soluble formulation of odorants and flavorings comprising at least one synthetically prepared odorant and flavoring, in which the odorants and flavorings are embedded homogeneously in a polymer matrix based on polyvinyllactams.

8 Claims, 1 Drawing Sheet

Figure 1: Release of Geraniol Extra at 40°C over 28 days
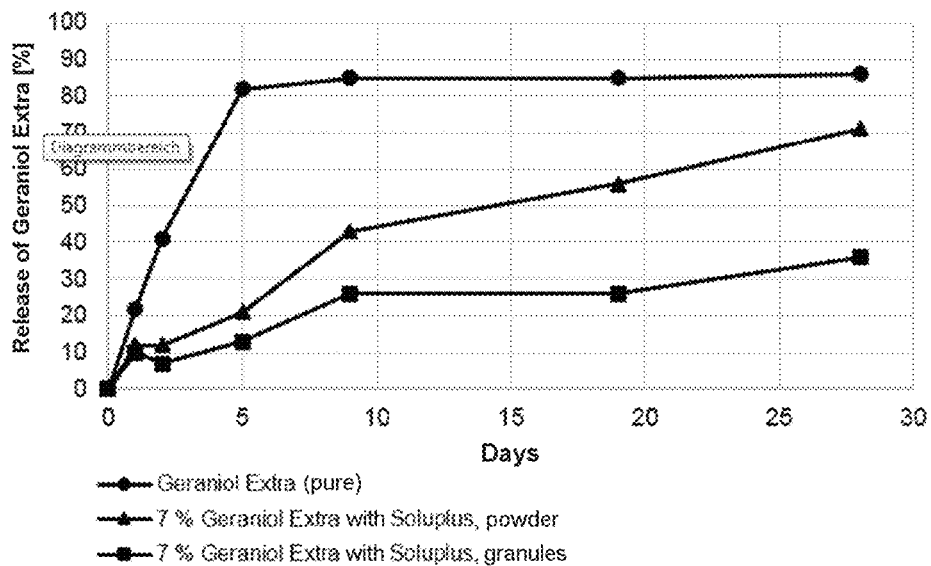
Figure 2: Release of L-menthol at 40°C over 28 days
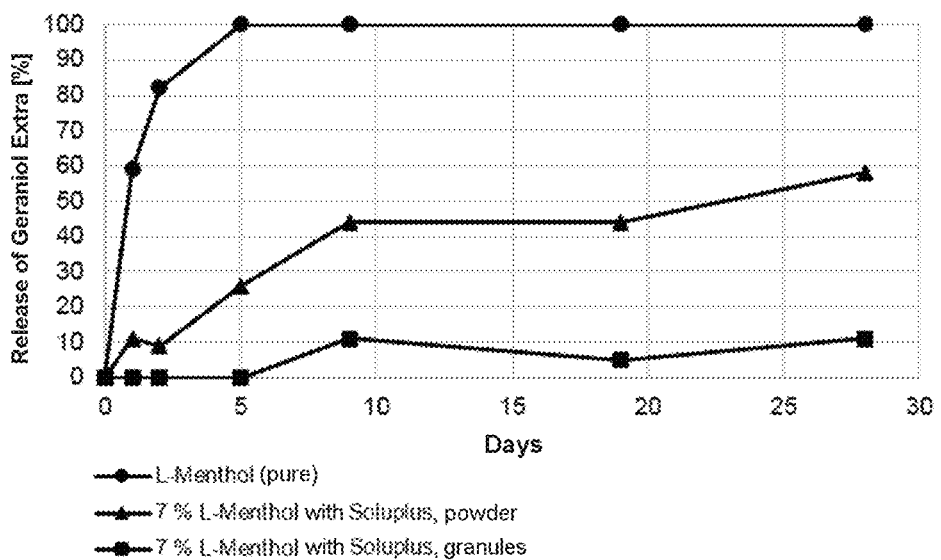

SOLID SOLUTIONS OF ODORIFEROUS SUBSTANCES AND FLAVORING AGENTS WITH VINYL LACTAM POLYMERS

CROSS REFERENCE TO RELATED APPLICATIONS

This is the U.S. national phase of International Application No. PCT/EP2016/074566, filed Oct. 13, 2016, which claims the benefit of European Patent Application No. 15191156.7, filed Oct. 23, 2015.

The present invention relates to water-soluble formulations of odorants and flavorings in which the odorants and flavorings are embedded homogeneously in a polymer matrix based on polyvinyllactams. The invention further relates to the use of such formulations.

The formulation of odorants and flavorings is not simple owing to the physicochemical properties of these substances. On the one hand they are often highly volatile, which makes processing at relatively high temperature difficult, and on the other hand they are often sparingly soluble in water, which means that they can be incorporated into aqueous systems only in an insufficient amount. Due to their diffusivity, they diffuse in compartmentalized formulations into regions in which they should not be present or are not present at the desired concentration. This is also a problem in the case of so-called microencapsulated systems. The controlled release of odorants and flavorings is in general a difficult and unsatisfactorily resolved problem.

Fatty and wax-like substances are frequently used for the formulation of odorants and flavorings, as described in US 2005/0227905. However, these have the disadvantage that they have a low melting point and are therefore sensitive to temperature and pressure. In addition, these substances are insoluble in water, and so small amounts of odorants and flavorings pass into the aqueous phase on dissolution in aqueous media and unattractive solid residues also remain.

The same is true of the formulations described in US 2009/0301504 A1, which also describes waxes, fats, sterols or polyethylene glycol in combination with other substances such as surfactants.

A further problem is the stability of the formulations in relation to environmental influences. Undesirable discolorations often occur due to decomposition of the odorants and flavorings. Also undesirable is a phase separation of the formulations, which can lead to bleeding of the odorants and flavorings.

In addition to this, the odorants and flavorings often cannot be readily processed due to their physical properties. Masses that are very prone to form lumps are frequently formed.

It was object of the present invention to find water-soluble formulations of odorants and flavorings which permit a controlled release over time of the odorants. Furthermore, the formulations should be easy to handle even during processing. The formulations should also be stable to environmental influences in order to prevent undesirable discolorations or modifications of the odorant or flavor profile in order to maintain as far as possible crystal clear formulations having a low color value. Furthermore, the odorants and flavorings should be protected against bleeding out of the formulation or diffusion into undesired areas.

Accordingly, optically clear, solid water-soluble formulations of odorants and flavorings have been found, comprising at least one synthetic flavoring, in which the odorants and flavorings are embedded homogeneously in a polymer matrix based on polyvinyllactams.

In accordance with the invention, "water-soluble" means that 10 g of substance/liter of water can be dissolved under standard conditions (20° C., 0.101325 MPa).

The formulations according to the invention are optically clear, which means that no phase separation can be observed under a light microscope with a 40-fold magnification.

Furthermore, the formulations according to the invention are colorless or only slightly colored. This means that the color value of a 1% preparation of the formulation in water is not greater than B5, BYS, Y5, GYS, R5 in accordance with the European Pharmacopoeia. The color is preferably not more intense than B6, BY6, Y6, GY6, R6.

The formulations are preferably in the form of solid solutions of the odorants and flavorings in the polymer matrix based on polyvinyllactams. The term "solid solutions" is known to those skilled in the art and refers to embedding of the odorants and flavorings in the polymer matrix by dispersion at the molecular level.

Odorants and flavorings of varying type and number can be incorporated, at least one synthetic odorant being present in the formulations according to the invention. In this case it is possible to use individual synthetic odorants such as geraniol, linalool, linalyl acetate, pyranol, geranyl acetate, anisaldehyde, citral, citronellal, lysmeral, citronellol, rose oxide, tetrahydrolinalool, hydroxycitronellal, beta-ionone, menthol, cinnamaldehyde, anethole, vanillin, eugenol, carvone and piperonal. Furthermore, in addition to a synthetic odorant and flavoring, essential oils such as cinnamon oil up to complex perfume or flavoring compositions may be added. Particular preference is given to linalool, geraniol and menthol.

The polyvinyllactams used may be homopolymers of vinylpyrrolidone, vinylcaprolactam, vinylformamide, vinylacetamide and also copolymers of vinyllactams with vinyl esters. Suitable vinyl esters are, for example, vinyl acetate, vinyl propionate or vinyl butyrate. In order to obtain water solubility of the copolymers, the proportion of vinyl ester monomers should be less than 50 wt %. A particularly suitable copolymer is a polymer obtained from 60 wt % N-vinylpyrrolidone and 40 wt % N-vinyl acetate.

Particular preference is given to graft copolymers of vinyllactams and/or vinyl esters on polyethers. A particularly suitable polymer is a graft copolymer of vinylcaprolactam and vinyl acetate on polyethylene glycol.

Particular preference is given to using graft copolymers obtainable from
  i) 50 to 60 wt % N-vinyllactam, preferably N-vinylcaprolactam
  ii) 25 to 35 wt % vinyl acetate, and
  iii) 10 to 20 wt % of a polyether, preferably polyethylene glycol,
with the proviso that the sum of components i), ii) and iii) is equal to 100 wt %.

Very particular preference is given to a graft copolymer of 13 wt % polyethylene glycol MW 6000, 57 wt % N-vinylcaprolactam and 30 wt % vinyl acetate, having an average molecular weight of 44 000 daltons.

General methods of producing the graft copolymers according to the invention are known per se. The production is effected by free-radically initiated polymerization, preferably in solution in non-aqueous organic solvents or in mixed non-aqueous/aqueous solvents. Suitable production methods are described, for example, in WO 2007/051743 and WO 2009/013202, the disclosure of which with respect to the production method is expressly incorporated by way of reference.

It is also possible to use mixtures of the polymers mentioned. The molecular weight of the polymers may be between 5000 and 1 000 000 daltons, preferably between 10 000 and 500 000 daltons and particularly preferably between 20 000 and 150 000 daltons.

The amount of odorants and flavorings in the polymer matrix is guided on the one hand by the type of odorants and flavorings, the individual intensity of which may be very different, and on the other hand by the type of application of the formulations.

Further additives which may be used are: dyes and pigments, plasticizers, stabilizers, preservatives, emulsifiers, solubilizers, surface-active substances, wetting agents, substances for adjusting viscosity, antioxidants.

The preparations according to the invention are preferably produced by melt extrusion, i.e. the odorant and flavoring is heated together with the polymer to above the glass transition temperature, mixed, kneaded and pressed through a nozzle. Subsequently, granules, powders, film pieces, i.e. various forms, can be produced from the extruded strands, strips or films. Surprisingly, the odorants and flavorings do not escape during the process and also do not decompose, even though the process is conducted at relatively high temperatures. The customary temperature range is between 70 and 250° C., preferably between 80 and 200° C. and more preferably between 90 and 170° C.

In addition to extruders, kneaders or injection-molding machines may also be used.

A suitable alternative production method is spray-drying, either from aqueous or organic solvent. Film drawing processes may also be used.

The degree of loading of the preparations of odorants or flavorings according to the invention is between 1 and 50%, preferably between 5 and 40% (m/m).

It has been found, surprisingly, that polyvinyllactams are capable of absorbing and binding odorants and flavorings, forming clear glassy formulations which can be used in many ways and also further processed. These glassy preparations dispense the odorant and flavoring in a retarded manner. A particular characteristic of these glassy preparations is that virtually no porosity is present and as a result the apparent density is close to the true density. The odorants and flavorings are therefore completely enclosed and are highly protected, particularly from oxygen and moisture.

If the preparation is brought into an aqueous medium, the odorant and flavoring is converted to the aqueous phase and is also kept there in solution above its saturation solubility in water. By means of micelle formation using an amphiphilic polymer, a pronounced retardation effect can also be achieved, that is to say that the odorant is released only in a time-delayed manner from the aqueous medium or, expressed in other words, the solution is odorous for much longer. The odorants and flavorings have a high affinity for polyvinyllactams and may be incorporated as a solid solution. The resulting preparations are very stable in solid form and the polymers are not hydrolyzed even in aqueous form.

The preparations according to the invention have very many uses. For instance, they can be used as additives for detergents and dishwashing compositions, as cosmetic additives, in pharmaceuticals or food supplements, in food or for releasing fragrances in rooms and in cars, in room humidifiers, in fragrance solutions etc.

The release of the odorants and flavorings may be determined in accordance with a preferred embodiment of the invention via the weight loss of the formulation over time, particularly under thermal stress.

The release of odorants and flavorings from the formulations according to the invention can also be monitored by gas chromatography analysis of the headspace via samples of the corresponding formulations.

According to one embodiment, the determination may be carried out as described hereinafter. In a temperature-controlled measuring chamber through which a controlled gas stream flows, e.g. air or nitrogen or other inert gases, at a controlled temperature and humidity, into which samples of the formulation have been introduced in a suitable manner, a defined volume of the offgas stream can be passed through a suitable adsorbent within certain time intervals. The odorant or flavoring content can subsequently be determined by gas chromatography after thermal desorption.

According to another embodiment, samples of the formulation according to the invention are introduced in a suitable manner into open beaded-edge vials. The beaded-edge vials are sealed after certain time intervals and the remaining odorant and flavoring content can be determined in the headspace above the sample by suitable methods such as headspace chromatography or solid phase microextraction with subsequent gas chromatography.

EXAMPLES

The polymer used was a graft copolymer of 13 wt % polyethylene glycol MW 6000, 57 wt % N-vinylcaprolactam and 30 wt % vinyl acetate, having an average molecular weight of 44 000 daltons, commercially available under the name of Soluplus®, BASF.

The melt extrusion was carried out using a Thermofischer Pharma 11 twin screw extruder, L/D ratio 40, screw diameter 11 mm.

The clarity was determined by means of a light microscope using a 40-fold magnification.

The color was determined according to the European Pharmacopoeia 8th Edition.

Example 1

The formulation of polymer (solid) with 13% (w/w) linalool (liquid) was extruded under the following conditions:
polymer metering unit: 300 g/h
linalool liquid metering rate: 45 g/h
temperature of zones 5-7: 120° C.
temperature of zone 8: 130° C.
screw speed 200 rpm
nozzle diameter 2 mm
nozzle pressure: 5 bar
torque: 6.9 Nm
Appearance: clear colorless extrudate, soluble in water; on dissolution in water, an odor of linalool odor is perceptible. Color not more intense than B6, BY6, Y6, GY6, R6.

Example 2

The formulation of polymer (solid) with 22% (w/w) linalool (liquid) was extruded under the following conditions:
polymer metering unit: 300 g/h
linalool liquid metering rate: 84 g/h
temperature of zones 5-7: 120° C.
temperature of zone 8: 130° C.
screw speed 200 rpm nozzle diameter 2 mm
nozzle pressure: 2 bar
torque: 6.9 Nm
Appearance: clear colorless extrudate, soluble in water; on dissolution, an odor of linalool is perceptible. Color not more intense than B6, BY6, Y6, GY6, R6.

Example 3

The formulation of polymer (solid) with 7% (w/w) Geraniol Extra (liquid) was extruded under the following conditions:
polymer metering unit: 500 g/h
Geraniol Extra liquid metering rate: 39 g/h
temperature of zones 5-8: 130° C.
screw speed 200 rpm
nozzle diameter 2 mm
nozzle pressure: 16 bar
torque: 7.0 Nm
Appearance: clear colorless extrudate, soluble in water; on dissolution in water, an odor of Geraniol Extra is perceptible. Color not more intense than B6, BY6, Y6, GY6, R6.

Example 4

The formulation of polymer (solid) with 13% (w/w) Geraniol Extra (liquid) was extruded under the following conditions:
polymer metering unit: 300 g/h
Geraniol Extra liquid metering rate: 45 g/h
temperature of zones 5-7: 120° C.
temperature of zone 8: 130° C.
screw speed 200 rpm
nozzle diameter 2 mm
nozzle pressure: 11 bar
torque: 7.3 Nm
Appearance: clear colorless extrudate, soluble in water; on dissolution in water, an odor of geraniol is perceptible. Color not more intense than B6, BY6, Y6, GY6, R6.

Example 5

The formulation of polymer (solid) with 20% (w/w) Geraniol Extra (liquid) was extruded under the following conditions:
polymer metering unit: 300 g/h
Geraniol Extra liquid metering rate: 75 g/h
temperature of zones 5-7: 120° C.
temperature of zone 8: 130° C.
screw speed 200 rpm
nozzle diameter 2 mm
nozzle pressure: 8 bar
torque: 7.0 Nm
Appearance: clear extrudate, soluble in water; on dissolution in water, an odor of geraniol is perceptible. Color not more intense than B6, BY6, Y6, GY6, R6.

Example 6

The formulation of polymer (solid) with 7% (w/w) L-menthol (melting of the solid menthol with subsequent liquid metering into the extrusion process) was extruded under the following conditions:
polymer metering unit: 500 g/h
L-menthol liquid metering rate: 38 g/h
temperature of zones 5-8: 140° C.
screw speed 200 rpm
nozzle diameter 2 mm
nozzle pressure: 24 bar
torque: 6.3 Nm
Appearance: clear extrudate, soluble in water; on dissolution in water, an odor of L-menthol is perceptible. Color not more intense than B6, BY6, Y6, GY6, R6.

Example 7 (Comparative Example)

Physical mixtures were prepared of polymer and in each case 5 wt %, based on weight of polymer, of odorant (L-menthol (solid), linalool (liquid) and Geraniol Extra (liquid)), in a Turbula T 2C mixer from Willy A. Bachofen AG (Basle) at 22 rpm for 10 minutes. In this case, the polymer was initially charged and the odorant added in portions.

On mixing the components, very highly sticky and lumpy masses were formed. A homogeneous formulation could not be produced in this manner.

Test 1

Determination of the Volatility of the Odorants and Flavorings from the Formulations at 40° C.:

Extruded polymer, formulations and an equivalent amount of odorant were weighed into separate dry bowls and stored at a constant temperature of 40° C., and the mass loss was determined at defined time points using an analytical balance. See also FIGS. 1 and 2

| Formulation | Start | 3 days | 7 day | 17 day | 26 day |
|---|---|---|---|---|---|
| Extruded Soluplus powder (160° C., 200 rpm, 1 kg) | 100.0 | 100.7 | 100.2 | 100.6 | 100.4 |
| Extruded Soluplus granules (160° C., 200 rpm, 1 kg) | 100.0 | 100.6 | 100.0 | 100.4 | 100.2 |

Calculation of Released Odorant and Flavoring after Days:

| Formulation | Start | 1 day | 2 days | 5 days | 9 days | 19 days | 28 days |
|---|---|---|---|---|---|---|---|
| Geraniol Extra (pure) | 0 mg | 33 mg | 62 mg | 123 mg | 127 mg | 128 mg | 129 mg |
| 7% Geraniol Extra with Soluplus, powder | 0 mg | 15 mg | 15 mg | 27 mg | 55 mg | 72 mg | 91 mg |
| 7% Geraniol Extra with Soluplus, granules | 0 mg | 12 mg | 8 mg | 16 mg | 32 mg | 32 mg | 44 mg |
| L-Menthol (pure) | 0 mg | 83 mg | 115 mg | 141 mg | 141 mg | 141 mg | 141 mg |
| 7% L-menthol with Soluplus powder | 0 mg | 12 mg | 10 mg | 29 mg | 50 mg | 50 mg | 65 mg |
| 7% L-menthol with Soluplus granules | 0 mg | 0 mg | 0 mg | 0 mg | 14 mg | 7 mg | 14 mg |

-continued

| Formulation | Start | 1 day | 2 days | 5 days | 9 days | 19 days | 28 days |
|---|---|---|---|---|---|---|---|
| Geraniol Extra (pure) | 0% | 22% | 41% | 82% | 85% | 85% | 86% |
| 7% Geraniol Extra with Soluplus, powder | 0% | 12% | 12% | 21% | 43% | 56% | 71% |
| 7% Geraniol Extra with Soluplus, granules | 0% | 10% | 7% | 13% | 26% | 26% | 36% |
| L-Menthol (pure) | 0% | 59% | 82% | 100% | 100% | 100% | 100% |
| 7% L-menthol with Soluplus powder | 0% | 11% | 9% | 26% | 44% | 44% | 58% |
| 7% L-menthol with Soluplus granules | 0% | 0% | 0% | 0% | 11% | 5% | 11% |

Test 2
Sustained Release of Odorants and Flavorings Due to Different Dissolution Rate of the Formulations:

Weigh an appropriate amount of formulation (aroma concentration corresponds to 100% of the saturation solubility of the aromas in water) into a 25 mL glass beaker. Add 25 mL of demineralized water and determine the dissolution rate (complete dissolution of the formulation) at room temperature while stirring.

Saturation Solubility of the Odorants and Flavorings in Water:

| Geraniol Extra | 0.10 g/L corresponds to 2.5 mg/25 mL |
|---|---|
| L-Menthol | 0.397 g/L corresponds to 9.925 mg/25 mL |

| Formulation | Initial weight in 25 mL of demineralized water | Dissolution rate in minutes |
|---|---|---|
| 7% Geraniol Extra with Soluplus powder | 38 mg | 17 |
| 7% Geraniol Extra with Soluplus granules | 36 mg | 65 |
| 7% L-menthol with Soluplus powder | 145 mg | 33 |
| 7% L-menthol with Soluplus granules | 142 mg | 85 |

The invention claimed is:

1. An optically transparent, solid water-soluble formulation of odorants and flavorings consisting of (a) at least one synthetically prepared odorant and flavoring and (b) a polymer matrix based on a graft copolymer of (i) 50 to 60 wt % N-vinyllactam, (ii) 25 to 35 wt % vinyl acetate, and (iii) 10 to 20 wt % of a polyether, with the proviso that the sum of components i), ii), and iii) is equal to 100 wt %, in which the at least one odorant and flavoring is embedded homogeneously in the polymer matrix,
wherein the at least one odorant and flavoring is present in a total amount of 7 to 22 wt %,
and wherein the at least one odorant and flavoring is embedded homogeneously in the polymer matrix in a form of a solid solution.

2. The water-soluble formulation according to claim 1, comprising a polymer matrix based on a graft copolymer of 13 wt % polyethylene glycol MW 6000, 57 wt % N-vinylcaprolactam, and 30 wt % vinyl acetate, having an average molecular weight of 44 000 daltons.

3. The water-soluble formulation according to claim 1 comprising, as odorants and flavorings, a substance selected from the group consisting of geraniol, linalool, linalyl acetate, pyranol, geranyl acetate, anisaldehyde, citral, citronellal, lysmeral, citronellol, rose oxide, tetrahydrolinalool, hydroxycitronellal, betaionone, menthol, essential oils, cinnamaldehyde, anethole, vanillin, eugenol, cinnamon oil, carvone, piperonal, and complex perfume or flavoring compositions.

4. The water-soluble formulation according to claim 1 comprising, as odorants and flavorings, a substance selected from the group consisting of geraniol, linalool, linalyl acetate, pyranol, geranyl acetate, anisaldehyde, citral, citronellal, lysmeral, citronellol, rose oxide, tetrahydrolinalool, hydroxycitronellal, betaionone, menthol, cinnamaldehyde, anethole, vanillin, eugenol, carvone, and piperonal.

5. The water-soluble formulation according to claim 1 obtained by melt extrusion.

6. The water-soluble formulation according to claim 1 for use as an additive for detergent and dishwashing compositions, as a cosmetic additive, in a pharmaceutical or a food supplement, in a food, or for releasing an odorant in buildings and vehicles.

7. The water-soluble formation according to claim 1 wherein the N-vinyllactam is N-vinylcaprolactam.

8. The water-soluble formation according to claim 1 wherein the polyether is polyethylene glycol.

* * * * *